(12) United States Patent
Miehe et al.

(10) Patent No.: US 8,455,469 B2
(45) Date of Patent: Jun. 4, 2013

(54) USE OF NORGESTIMATE AS A SELECTIVE INHIBITOR OF TRPC3, TRPC6 AND TRPC7 ION CHANNELS

(75) Inventors: Susanne Miehe, Frankfurt am Main (DE); Heinz-Werner Kleemann, Frankfurt am Main (DE); Carsten Struebing, Frankfurt am Main (DE)

(73) Assignee: Sanofi, Paris (FR)

( * ) Notice: Subject to any disclaimer, the term of this patent is extended or adjusted under 35 U.S.C. 154(b) by 276 days.

(21) Appl. No.: 12/738,137

(22) PCT Filed: Oct. 14, 2008

(86) PCT No.: PCT/EP2008/008671
§ 371 (c)(1),
(2), (4) Date: Sep. 14, 2010

(87) PCT Pub. No.: WO2009/052972
PCT Pub. Date: Apr. 30, 2009

(65) Prior Publication Data
US 2011/0015167 A1    Jan. 20, 2011

(30) Foreign Application Priority Data
Oct. 26, 2007    (EP) ..................................... 07291301

(51) Int. Cl.
*A61K 31/56*    (2006.01)
*C12N 11/04*    (2006.01)
*H01L 21/331*    (2006.01)

(52) U.S. Cl.
USPC ........................... 514/182; 435/475; 435/7.21

(58) Field of Classification Search
USPC ......................................... 514/182; 435/475
See application file for complete search history.

(56) References Cited

U.S. PATENT DOCUMENTS

| 2001/0044584 | A1 | 11/2001 | Kensey |
| 2003/0119796 | A1 | 6/2003 | Strony |
| 2005/0096303 | A1* | 5/2005 | Mayerhofer .................. 514/177 |

FOREIGN PATENT DOCUMENTS

| WO | WO 2004/041289 | 5/2004 |
| WO | WO 2006/074802 | 7/2006 |
| WO | WO2006074802 | * 7/2006 |
| WO | WO 2006/102596 | 9/2006 |

OTHER PUBLICATIONS

Inoue et al. (Circ Res. 2006;99:119-131).*
International Search Report for WO2009/052972 dated Apr. 30, 2009.
Zhu et al., Molecular cloning of a widely expressed human homologue for the *Drosophila* trp gene, FEBS Letters, vol. 373, 1995, pp. 193-198.
Ackerman et al., Ion-Channels—Basic Science and Clinical Disease, New England J. of Medicine, vol. 336. 1997, pp. 1575-1595.
Dietrich et al., In vivo TRPC functions in the cardiopulmonary vasculature, Cell Calcium, vol. 42, No. 2, Aug. 2007, pp. 233-244.
Bigay et al., Fluoride complexes of aluminum or beryllium act on G-proteins as reversibly bound analogues of the y phosphate of GTP, The EMBO J. vol. 6, No. 10, 1987, pp. 2907-2913.
Boulay et al., Phagocyte Chemoattractant Receptors, Annals of NY Academy of Sciences, 1997, pp. 69-84.
Clapham, D., Sorting out MIC, TRP, and CRAC Ion Channels, J. Gen. Physiol, 2001, pp. 1-4.
Daniel et al., Screening for Potassium Channel Modulators by a High-Through-Put 86-Rubidium Efflux Assay in a 96-Well Microtiter Plate, J. Pharmacol. Meth. vol. 25, 1991, pp. 185-193.
Dietrich et al., Another TRP to Endothelial Dysfunction TRMP2 and Endothelial Permeability, Circulation Research, Feb. 15, 2008, pp. 275-277.
Dietrich et al., Increased Vascular Smooth Muscle Contractility in TRPC6-1-Mice, Molecular and Cellular Biology, vol. 25, No. 16, Aug. 2005, pp. 6980-6989.
Freichel et al., Functional role of TRPC proteins in native systems: implications from knockout and knock-down studies, J. Physiol., 2001, pp. 59-66.
Hamill et al., Improved Patch-Clamp Techniques for High-Resolution Current Recording from Cells and Cell-Free Membrane Patches, Pflugers Arch vol. 391, 1981, pp. 85-100.
He et al., The Tricorned Ser/Thr Protein Kinase is Regulated by Phosphorylation and interacts with Furry during *Drosophila* Wing Hair Development, Molecular Biology of the Cell, vol. 16, Feb. 2005, pp. 689-700.
Hoffman et al., Phylogenetic Perspectives in Innate Immunity, Science, vol. 284, May 21, 1999, pp. 1313-1318.
Holevinsky et al., ATP-sensitive K+ Channel Opener Acts as a Potent Cl-Channel Inhibitor in Vascular Smooth Muscle Cells, J. Membrane Biol. vol. 137, 1994, pp. 59-70.
Jung et al., TRPC6 is a candidate channel involved in receptor-stimulated cation currents in A7r5 smooth muscle cells, Am. J. Physiol. Cell Physiol. vol. 282, 2002, pp. C347-C359.
Kawabata et al., Evaluation of Proteinase-Activated Receptor-1 (PAR1) Agonists and Antagonists Using a Cultured Cell Receptor Desensitization Assay: Activation of PAR2 by PAR1—Targeted Ligands, J. of Pharm. & Exp. Theraputics, vol. 288, No. 1, 1999, pp. 358-370.
Kim et al., Differential expression of uterine calcium transporter1 and plasma membrante Ca2+ ATPase ib during rat estrous cycle, Am. J. Physiol Endocrinol Metab vol. 291, 2006, pp. E234-E241.
Kraft, R., The Na+/Ca2+ exchange inhibitor KB-R7943 potently blocks TRPC channels, Biochem & Biophys Res. Comm. vol. 361, 2007, pp. 230-236.

(Continued)

*Primary Examiner* — Shirley V Gembeh
(74) *Attorney, Agent, or Firm* — Nicole L. M. Parsons (57) ABSTRACT

TRPC ion channels are non-selective channels widely expressed in human tissues. These channels are involved in numerous physiological functions and are putative targets for the development of novel medicines. There is a need to gain a better understanding of TRPC ion channels in cells and beyond. The present invention provides a pharmacological tool compound that allows to study TRPC ion channels due to its discriminating inhibition of TRPC subfamilies. In the present invention, norgestimate is shown to selectively inhibit TRPC3, TRPC6 and TRPC7.

10 Claims, 5 Drawing Sheets

OTHER PUBLICATIONS

Li et al., Determining the functional role of TRPC channels in primary cells, Pflugers Arch—Eur J Physiol vol. 451, 2005, pp. 43-52.

Lucky et al., Effectiveness of norgestimate and ethinly estradiol in treating moderate acne vulgaris, J. of Amer. Acad. of Derm. vol 37, No. 5, Pt 1., Nov. 1997, pp. 746-754.

Mattox et al., Combined oral hormone therapy formulations, Database Medline [Online] US National Library of Medicine, Bethesda, MD, US. Aug. 2001, Database accession No. NLM11521121.

Montell, C., Physiology, Phylogeny, and Functions of the TRP Superfamily of Cation Channels, Sciences' STKE, Jul. 10, 2001, pp. 1-17.

Montell, C., The TRP Superfamily of Cation Channels, Sciences' STKE, Feb. 22, 2005, pp. 1-24.

Moran et al., Genome sequence of Silicibacter pomeroyi reveals adaptations to the marine environment, Nature, vol. 432, Dec. 16, 2004, pp. 910-913.

O'Neil et al., The Merck Index—An Encyclopedia of Chemicals, Drugs and Bioiogicais, 13th Edition, 2001, , Merck Research Laboratories, NJ USA, p. 1201, col. 1, paragraph 6735—col. 2.

Okada et al., Molecular and Functional Characterization of a Novel Mouse Transient Receptor Potential Protein Homologue TRP7, J. of Biol. Chem., vol. 274, No. 39, 1999, pp. 27359-27370.

Okuhara et al., Transient receptor potential channels as drug targets, Expert Opin. Ther. Targets, vol. 11, No. 3, 2007, pp. 391-401.

Olson et al., The duration of response to norgestimate and ethinyl estradiol in the treatment of acne vulgaris, Int. J. of Fertility and Women's Medicine, vol. 43, No. 6, Nvo. 1998, pp. 286-290.

Schaefer, M., Homo- and heteromeric assembly of TRP channel subunits, Pflugers Arch vol. 451, 2005, pp. 35-42.

Soboloff et al., Role of Endogenous TRPC6 Channels in Ca2+ Signal Generation in A7r5 Smooth Muscle Cells, J. of Biol. Chem., vol. 280, No. 48, Dec. 2, 2005, pp. 39786-39794.

Sternweis et al., Aluminum: A requirement for activation of the regulatory component of adenylate cyclase by fluoride, PNAS, vol. 76, 1982, pp. 4888-4891.

Vestergaard-Bogind et al., Single-File Diffusion through the Ca2+Activated K+ Channel of Human Red Cells, J. of Membrane Biology, vol. 88, 1985, pp. 67-75.

Ward et al., Tidl interacts with TRPCS and negatively regulated calcium entry in cardiomyocytes, Database Blosis [Online] Biosciences Information Service, Phil., PA, Oct. 16, 2007 Abstact.

Wes et al., TRPC1, a human homolog of a *Drosophila* store-operated channel, PNAS, vol. 92, Oct. 1995 pp. 9652-9656.

Xu et al., Block of TRPC5 channels by 2-aminoethoxydiphenyl borate: a differential, extracellular and voltage-dependent effect, Br. J. of Pharmacology, vol. 145, 2005, pp. 405-414.

Ylikorkala et al., Effects on serum lipid profiles of continuous 17beta-estradiol intermittent norgestimage regimens versus continuous combined 17beta-estradiol/noresthisterone acetate hormone replacement therapy, Clinical Therapeutics, vol. 22, No. 5, May 2000, pp. 622-636.

\* cited by examiner

USE OF NORGESTIMATE AS A SELECTIVE INHIBITOR OF TRPC3, TRPC6 AND TRPC7 ION CHANNELS

FIELD OF THE INVENTION

The present invention relates to the use of norgestimate as a selective inhibitor of members of the TRPC3/6/7 ion channel subfamily, which allows to pharmacologically distinguishing between said subfamily members and members of other TRPC subfamilies. It also relates to the use of norgestimate to identify, characterize and modulate TRPC ion channels in cellular models, tissues or animal models.

BACKGROUND OF THE INVENTION

TRPC channels are nonspecific cation channels widely expressed in human tissues (Montell 2005). They were the first found mammalian homologues of *Drosophila* TRP (Wes et al., 1995, Zhu et al., 1995). Seven proteins, referred to as TRPC1-7, constitute the canonical (or classical) TRP subfamily that is the closest related to the archetypal *Drosophila* TRP (30-40% identity, Okuhara et al., 2007).

Based on amino acid sequence homology, tissue distribution and functional similarities, TRPCs can be subclassified into four groups (Clapham et al., 2001; Montell, 2001). Being quite unique within the TRPC family, TRPC1 and TRPC2 each constitute a subfamily by themselves while TRPC4 and -5 are merged just as TRPC3, -6, and -7. The closely related TRPC3, TRPC6 and TRPC7 channels share a common activation mechanism and diacylglycerol (DAG) has been identified as their endogenous ligand (Hofmann et al., 1999; Okada et al., 1999).

According to the WHO, 30% of all deaths worldwide were caused by various cardiovascular diseases in 2005. Thus, there is an immense medical need for new medicines that prevent and treat cardiovascular diseases. TRPC channels are considered important pharmacological targets for the development of novel medicines for several cardiovascular pathologies including cardiomyopathy, vascular remodelling, hypertension and high endothelial permeability (Dietrich et al., 2007).

But so far, there are many open questions regarding their native composition and activation mechanisms, physiological functions, and roles in pathophysiology and disease. In situ identification of native TRPC channels is complicated by their wide and partially overlapping distribution, potential heteromultimerization, similar electrophysiological properties and a paucity of tool compounds to unequivocally trace these channels (Moran et al., 2004).

Known TRPC organic inhibitors such as 2-aminoethoxydiphenyl borate (2-APB) {Xu et al., 2005}, SKF 96365 (Boulay et al., 1997; Zhu et al., 1998) and BTP2 (He et al., 2005), and inorganic blockers such as $Gd^{3+}$ and $La^{3+}$ are not potent and specific enough (Li et al., 2005).

Studies in transgenic mice already have proven to be valuable in unravelling possible physiological functions of certain TRPCs (Freichel et al., 2001). But these model systems do not exist for each of the seven mammalian TRPC channels so far, their generation and analysis is time- and cost-consuming and they also have limitations as they are vulnerable to compensatory effects by closely related channels (Dietrich et al., 2005c).

Thus, the aim of the present invention was to develop a new pharmacological tool that allows to discriminate between and within the TRPC subfamilies, thereby allowing to elucidate the roles of the different channels under physiological as well as patho-physiological conditions.

According to the present invention, this is achieved with the use of norgestimate to selectively inhibit TRPC3, TRPC6 and TRPC7. Thus, norgestimate allows to pharmacologically distinguishe channels belonging to different TRPC subfamilies. In addition, norgestimate does not interfere with the common G protein-coupled receptor, Gq, phospholipase Cβ pathway that mediates TRPC channel activation in many cells. These properties make norgestimate a preferable tool for the identification and modulation of TRPC3, TRPC6 and TRPC7.

SUMMARY OF THE INVENTION

One subject matter of the present invention is directed to the use of norgestimate as a selective inhibitor of a TRPC ion channel. A TRPC ion channel selectively inhibited by norgestimate is preferably TRPC3, TRPC6 or TRPC7. Norgestimate may be used to selectively inhibit a TRPC ion channel in vitro and in vivo.

Figure 1:
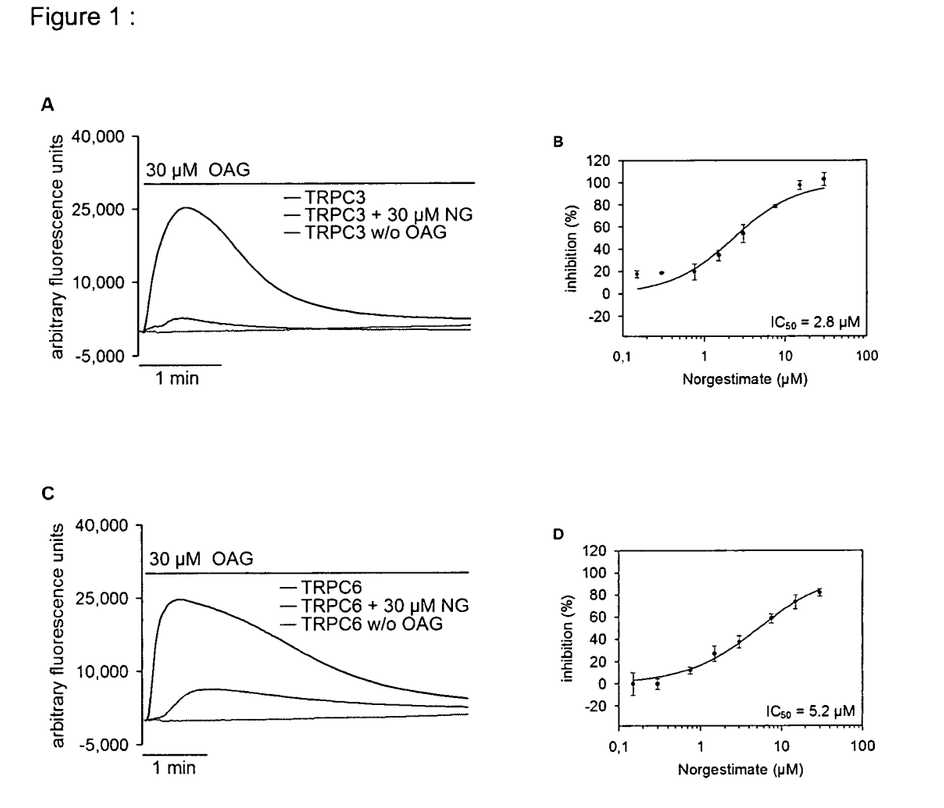
FIG. 1:
(A, C) Time-dependent changes of intracellular $Ca^{2+}$ concentration ($[Ca^{2+}]_i$) of fluo-4-loaded induced TRPC3 HEK293 cells (A) and TRPC6 HEK293 cells (C). TRPC-mediated $Ca^{2+}$ influx following application of 30 μM OAG was strongly reduced in cells preincubated with 30 μM norgestimate (NG).
Measurements were performed in 96er well plates using FLIPR (Molecular Devices, Sunnyvale, Calif., USA)
(B, D) Determination of norgestimates $IC_{50}$ value on TRPC3 (B) and TRPC6 (D). Data are represented as means of 2 wells (B) and 4 wells (D) with 45,000 cells per well.
Figure 2:
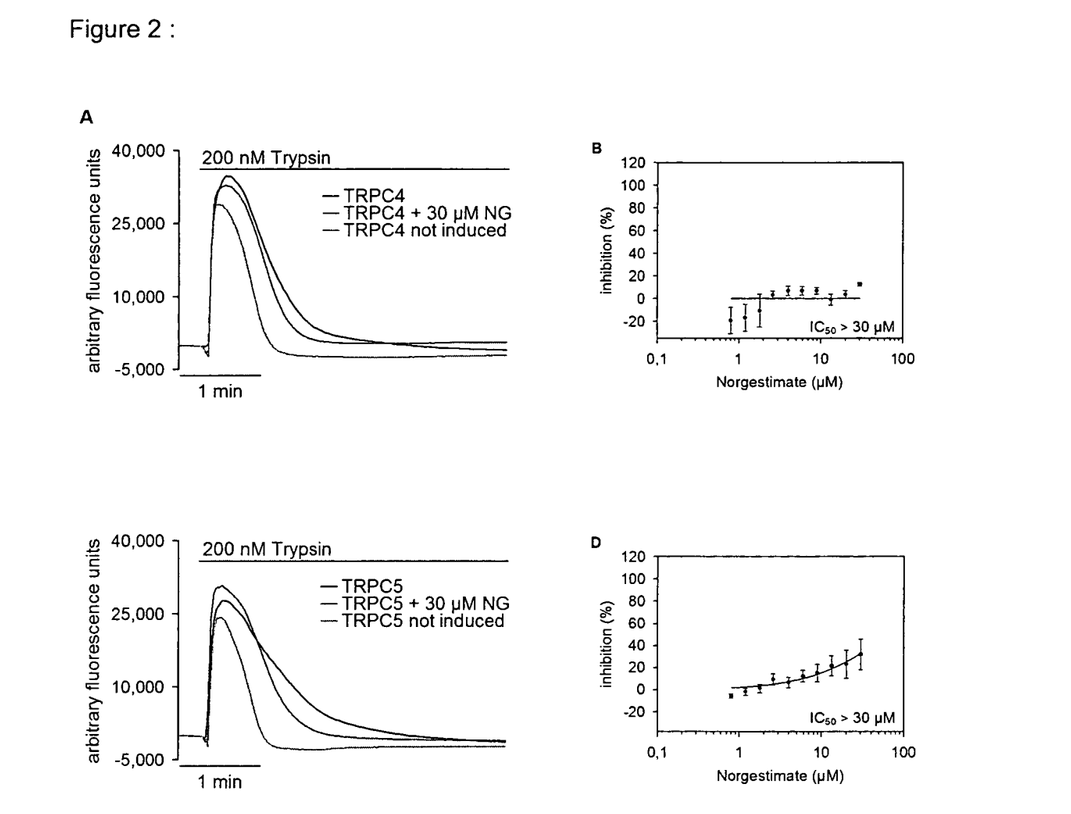
FIG. 2:
(A, C) Time-dependent changes of intracellular $Ca^{2+}$ concentration ($[Ca^{2+}]_i$) of fluo-4-loaded induced TRPC4 HEK293 cells (A) and TRPC5 HEK293 cells (C). TRPC-mediated $Ca^{2+}$ influx following application of 200 nM trypsin was slightly reduced in cells preincubated with 30 μM norgestimate (NG).
Measurements were performed in 96er well plates using FLIPR (Molecular Devices, Sunnyvale, Calif., USA)
(B, D) Determination of norgestimates $IC_{50}$ value on TRPC4 (B) and TRPC5 (D). Data are represented as means of 2 wells (B) and 4 wells (D) with 47,000 cells per well.

In particular, norgestimate is at least 4-fold more potent on TRPC3/6/7 subfamily members than on TRPC4/5 subfamily members (FIGS. 1 and 2). The 4-fold more potency of norgestimate on TRPC3/6/7 subfamily members than on TRPC4/5 subfamily members was evaluated with fluorometric measurements and based on the calculated inhibition by 10 µM norgestimate.

Figure 3:
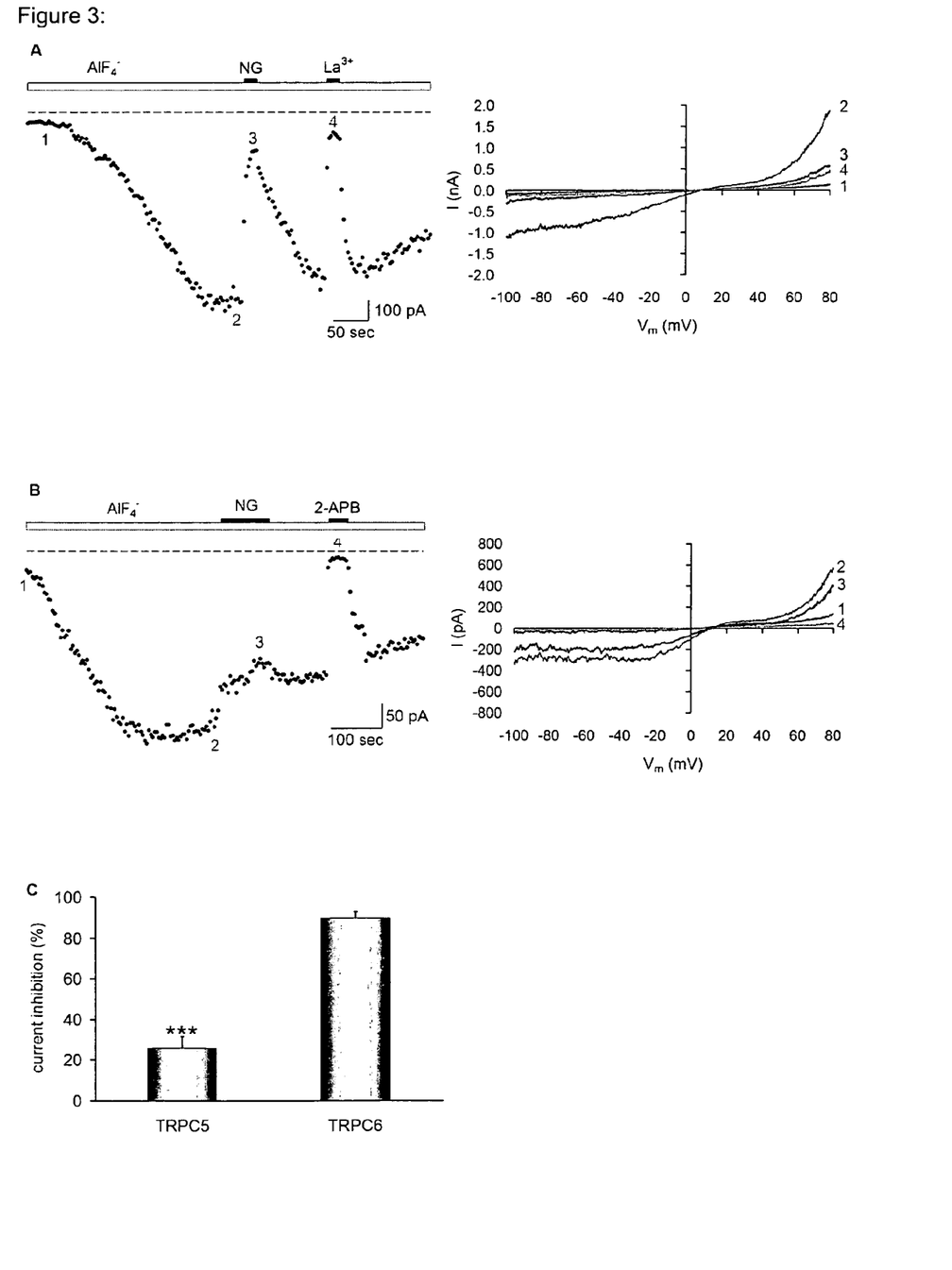
FIG. 3:
Effect of 10 μM norgestimate (NG) on whole-cell currents evoked by $AlF_4^-$ infusion into induced TRPC6— (A) and TRPC5 HEK 293 (B) cells. Whole cell currents recorded at −70 mV (left panels) and the corresponding current-voltage (I-V) relationships are shown (right panels). For background correction channels were completely blocked with 10 μM $La^{3+}$ (A) or 10 μM 2-APB (B). The curves were obtained during voltage ramps from −100 to +80 mV.
(C) Statistical analysis of the norgestimate effect on TRPC5— and TRPC6-mediated currents. 10 μM norgestimate inhibit 25.9±5.7% (n=20) of TRPC5-mediated currents and 89.9±3.1% (n=15) of TRPC6-mediated currents (P<0.001, Wilcoxon test, two-sided).

These fluorometric measurements were exemplary validated by means of patch clamp recording in the whole-cell configuration (FIG. 3).

As a selective inhibitor of TRPC3, TRPC6 and TRPC7, norgestimate may be used as a pharmacological tool which allows characterising channels belonging to different TRPC subfamilies, that is distinguishing between TRPC3/6/7 subfamily members and members of other TRPC ion channel subfamilies (FIGS. 1, 2 and 3).

As such an inhibitor, norgestimate may further be used as a tool compound to develop and verify assays that measure the activity of the respective ion channel. An example of such an assay is shown in FIG. 1.

Another subject matter of the present invention is directed to the use of norgestimate to make a differential analysis of the channel functions of, respectively, the TRPC3/6/7 subfamily members and the TRPC4/5 subfamily members under physiological and patho-physiological conditions. This can be done e.g. as described in the Exemplification. The analysis can be made in a cell, a tissue or an animal. The animal may be a rodent, preferably a mouse or a rat.

According to a preferred embodiment, the modulation of native TRPCs by norgestimate can be investigated using the A7r5 cell line, which is a validated model system for the study of endogenously expressed TRPC ion channels. Further details of such preferred assay systems are given in the Exemplification and in FIG. 4.

Another subject matter of the present invention is directed to a method of determining the effect of norgestimate on the TRPC channel activity. Preferred TRPC ion channels are TRPC3, TRPC6 and TRPC7.

In general, a cell expressing a TRPC ion channel is brought into contact with norgestimate and the influence of norgestimate on the TRPC ion channel activity is measured or detected.

Another subject matter of the present invention is directed to a method of identifying a TRPC ion channel modulator. Preferred TRPC ion channels are TRPC3, TRPC6 and TRPC7.

In general, a cell expressing a TRPC ion channel is brought into contact with a test compound and the influence of the test compound on the TRPC ion channel activity is measured or detected.

In preferred embodiments the cells used in the above methods are fluorescent cells.

Preferred cells according to the present invention are MDCK, HEK 293, HEK 293 T, BHK, COS, NIH3T3, Swiss3T3 or CHO cells, in particular a HEK293 cell.

TRPC channel activity can be measured or detected by measuring or detecting a change in ion fluxes, in particular $Ca^{2+}$ fluxes, by e.g. patch clamp techniques, whole cell currents, radiolabeled ion fluxes, or in particular fluorescence e.g. using voltage-sensitive dyes or ion-sensitive dyes (Vestergarrd-Bogind et al. (1988), J. Membrane Biol., 88:67-75; Daniel et al. (1991) J. Pharmacol. Meth. 25:185-193; Hoevinsky et al. (1994) J. Membrane Biol., 137:59-70; Ackerman et al. (1997), New Engl. J. Med., 336:1575-1595; Hamil et al. (1981), Pflugers. Archiv., 391:185).

An example for the measurement of the TRPC ion channel activity is an assay comprising the steps of:
(a) contacting a fluorescent cell expressing a TRPC ion channel,
(b) stimulating $Ca^{2+}$ influx by a channel activator before, simultaneously or after contacting the fluorescent cell with the modulator or test compound, and
(c) measuring or detecting a change in fluorescence.

Another subject of the present invention is directed to a method for profiling selectivity of norgestimate for a TRPC channel, which comprises assessing the norgestimate's ability to inhibit the TRPC channel activity and comparing the inhibition potency of norgestimate between and within the different TRPC subfamilies.

Another subject of the present invention is directed to the use of norgestimate in the preparation of a medicament for the treatment of cardiovascular diseases, coronary artery diseases, atherosclerosis, end-stage renal failure, neurological diseases, chronic pain, acute pain, or inflammatory diseases.

Norgestimate may be formulated with one or more pharmaceutically acceptable carriers or auxiliary substances. Pharmaceutically acceptable carriers or auxiliary substances are for example a physiological buffer solution, e.g. sodium chloride solution, demineralised water, stabilizers, such as protease or nuclease inhibitors, or sequestering agents, such as EDTA.

Another subject of the present invention is directed to a method of treatment of a cardiovascular disease, a coronary artery disease, atherosclerosis, end-stage renal failure, a neurological disease, chronic pain, acute pain, or an inflammatory disease, comprising administering to a subject a therapeutically effective amount of a composition comprising norgestimate.

DETAILED DESCRIPTION OF THE INVENTION

The term "TRPC ion channel" or "TRPC" in context of the present invention refers to $Ca^{2+}$ permeable non-selective cation channels. It shall mean any one of the list of the following transient receptor potential canonical ion channels: TRPC1, TRPC2, TRPC3, TRPC4, TRPC5, TRPC6 and TRPC7. Especially preferred are TRPC3, TRPC6 and/or TRPC7.

Such TRPC ion channels could be derived from any vertebrate and in particular mammalian species (e.g. dog, horse, bovine, mouse, rat, canine, rabbit, chicken, anthropoid, human or others). The TRPC could be isolated from tissue probes of such vertebrate organisms or could be manufactured by means of recombinant biological material that is able to express the TRPC protein.

The term may refer to native polypeptides, polymorphic variants, mutants, and interspecies homologues.

"Norgestimate" is also known under its chemical name D-17.beta.-acetoxy-B-ethyl-17.alpha. ethinyl-gon-4-en-3-one oxime. It is a gestagen which is a synthetic form of the naturally occurring female sex hormone progesterone. Norgestimate is a molecule used in the prior art in the composition of hormonal contraceptives. In the present invention, norgestimate is used as a selective inhibitor of a TRPC3, TRPC6 and TRPC7.

The term "selective inhibition" in context of the present invention refers to the potency of an inhibitor, e.g. norgestimate, to inhibit one or more members of the TRPC family with a higher efficiency than one or more other members. In a preferred embodiment, norgestimate is more effective on the TRPC3/6/7 subfamily than on the TRPC4/5 subfamily. In a more preferred embodiment, norgestimate is at least 4-fold more effective on the TRPC3/6/7 subfamily than on the TRPC4/5 subfamily.

The term "pharmacological tool" refers to a compound which functional properties allow to study how drugs interact with living organisms to produce a change in functions of interest, thereby allowing to study new drug composition and properties, interactions, toxicology, therapy, medical applications and antipathogenic capabilities. Furthermore, the term refers to a compound which may be used to characterize potential targets for the development of novel medicines, e.g. characterize their native composition, activation mechanisms, physiological functions, and roles in patho-physiology and disease.

The term "differential analysis" refers to an analysis which allows to characterize channel function differences between TRPC3/6/7 subfamily members and TRPC4/5 subfamily members under the same conditions.

According to a preferred embodiment, cells expressing respectively TRPC6 ion channels and TRPC5 ion channels are brought into contact with norgestimate in two parallel experiments, and the influence of norgestimate on the respective TRPC ion channel activities is measured or detected, allowing to compare functions of the respective channels under the same conditions.

The term "TRPC ion channel modulator" means a modulating molecule of the TRPC channel, in particular an inhibitory or activating molecule ("inhibitor" or "activator"), especially an inhibitor of the TRPC channel identifiable according to the method of the present invention.

An inhibitor is generally a compound which, e.g. binds to, partially or totally blocks activity, decreases, prevents, delays activation, inactivates, desensitizes, or down-regulates the activity or expression of at least one of the TRPC channels as preferably described above in details.

An activator is generally a compound which, e.g. increases, opens, activates, facilitates, enhances activation, sensitizes, agonizes, or up-regulates the activity or expression of at least one of the TRPC channels as preferably described above in details.

Such modulators include genetically modified versions of the TRPC channels, preferably an inactivating mutant of the TRPC channels, as well as naturally occurring or synthetic ligands, antagonists, agonists, peptides, cyclic peptides, nucleic acids, antibodies, antisense molecules, ribozymes, small organic molecules and the like.

Examples of TRPC activators are diacylglycerols, in particular 1-Oleyl-2acetyl-sn-glycerol (OAG), Gq-coupled receptor agonists, such as phenylephrine and in particular trypsin, an agonist that stimulates receptor tyrosine kinases such as epidermal growth factor (EGF) or diacylglycerol generating enzymes such as phospholipases or activators thereof.

An example for the measurement of the TRPC ion channel activity modulation in presence of a test compound is as following:

In general, cells are provided which express a TRPC channel. Such cells can be produced using genetic methods known to a person skilled in the art. After having induced the expression of the TRPC channel, cells are usually plated into e.g. microtiter plates and grown. Usually the cells grow at the bottom of multiwell plates and are fixed. Thereafter, the cells are generally washed and loaded with a dye in a suitable loading buffer, preferably with a fluorescent dye such as fluo4am. After having removed the loading buffer, the cells are incubated with the test compound or modulator, in particular with a biochemical or chemical test compound as described above, e.g. in the form of a chemical compound library. $Ca^{2+}$ measurements can be carried out using e.g. a Fluorescence Imaging Plate Reader (FLIPR). To stimulate $Ca^{2+}$ influx through the TRPC channel a channel activator such as OAG should generally be applied.

The expected effects of inhibitors would be a reduction of e.g. the fluorescence increase. Activators would lead to a further increase of e.g. an activator-evoked fluorescence or induce e.g. an activator-independent fluorescence increase.

Thereafter, suitable modulators, in particular inhibitors can be analyzed and/or isolated. For the screening of chemical compound libraries, the use of high-throughput assays are preferred which are known to the skilled person or which are commercially available.

The term "cell expressing TRPC" refers to a cell expressing the ion channel of interest endogenously or a recombinant cell.

The cell will usually be a mammalian cell, such as a human cell, a mouse cell, a rat cell, a Chinese hamster cell, etc. Cells that are found to be convenient include MDCK, HEK 293, HEK 293 T, BHK, COS, NIH3T3, Swiss3T3 and CHO cells, preferably HEK293 cells.

The term "tissue" as used herein, can refer to any type of tissue preparation or taken part of tissue or organ (e.g. brain, liver, spleen, kidney, heart, blood vessels, muscle, skin, etc. and refers also to any kind of body fluid such as blood, saliva, lymphatic fluid, synovial fluid etc.), preferably if derived from a vertebrate, and more preferably from a mammal such as a human. Tissue samples can be gained by well-known techniques, such as taking of blood, tissue punction or surgical techniques.

Examples of dyes used in such measurements are Di-4-ANEPPS (pyridinium 4-(2(6-(dibutylamino)-2-naphthalenyl)ethenyl)-1-(3-sulfopropyl)hydroxide), CC-2-DMPE (1,2-ditetradecanoyl-sn-glycero-3-phosphoethanolamine triethylammonium), DiSBAC2 (bis-(1,2-dibarbituric acid)-trimethine oxanol), DiSBAC3 ((bis-(1,3-dibarbituric acid)-trimethine oxanol), SBFI-AM (1,3-benzenedicarboxylic acid, 4,4'-[1,4,10-trioxa-7,13-diazacyclopentadecane-7,13-diylbis(5-methoxy-6,12-benzofurandiyl)]bis-(tetrakis-[(acetyloxy)methyl]ester)), fluo3am (1-[2-Amino-5-(2,7-dichloro-6-hydroxy-3-oxy-9-xanthenyl)phenoxy]-2-(2'-amino-5<1>-methylphenoxy)ethane-N,N,N',N'-tetraacetic), fluo4am (1-[2-Amino-5-(2,7-dichloro-6-hydroxy-4-oxy-9-xanthenyl)phenoxy]-2-(2'-amino-5'-methyl phenoxy) ethane-N,N,N',N'-tetraacetic) or fura2am (142-(5'-carboxy-oxazol-2'-yl)-6-aminobenzofuran-5-oxy]-2-(2'-amino-5<1>-methyl-phenoxy)-ethane-N,N,N',N'-tetraacetic).

The term "profiling" refers to the characterisation of a compound, e.g. norgestimate, through functional and structural categories, potency, specificity, selectivity and mechanism-of-action. In the present invention, it refers in particular to the selectivity study of the inhibition effect of norgestimate on a TRPC ion channel.

The term "medicament" refers to a composition comprising a therapeutically effective amount of norgestimate and one or more pharmaceutically acceptable carriers or auxiliary substances.

The medicament can be administered systemically or topically, in any conventional manner. This can e.g. be by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. It is further possible to administer the medicament topically and locally in order to treat the particular disease as described above, if appropriate, in the form of liposome complexes.

The medicament can also be administered in form of an injection solution or an infusion. Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The following Figures and Examples shall explain the present invention without limiting the scope of the invention.
Exemplification
1. FLIPR Measurements
TRPC3/6

TRPC3 and TRPC6 were directly activated by application of oleoyl-2-acetyl-sn-glycerol (OAG), a membrane permeable diacylglycerol analogue. TRPC3- and TRPC6-mediated $Ca^{2+}$ influx following application of 30 μM OAG was strongly reduced in cells preincubated with 30 μM norgestimate (FIG. 1A, C). The $IC_{50}$ of norgestimate on TRPC3 was 2.8±0.4 μM (n=2, FIG. 1B). Norgestimate was similarly active on TRPC6 with an $IC_{50}$ of 5.2±0.4 μM (n=4, FIG. 1 D).
TRPC4/5

When these experiments were performed, no direct physiological stimuli of TRPC4 and TRPC5 were known. Therefore, both channels had to be stimulated indirectly, e.g. by application of trypsin, a protease-activated receptor (PAR) stimulating protease. Trypsin is able to activate all four known PAR subtypes and the mRNA of three of them ($PAR_1$, $PAR_2$ and $PAR_3$) was shown to be endogenously present in HEK293 cells (Kawabata et al., 1999). PAR are G protein-coupled and their activation leads to calcium store depletion from endoplasmic reticulum (ER). This so called phosphatidylinositol (PI) response is independent of the channel's presence but consequently leads to activation of store-operated channels like TRPC4 and TRPC5. Basic prerequisite to measure the effect of norgestimate on both channels under these conditions is to exclude PAR antagonism of this potential channel inhibitor. Hence, calcium release from ER was compared in non-induced TRPC5 HEK293 FITR cells preincubated with 30 μM norgestimate or buffer only (10 min).

Kinetics and quantity of calcium store release in cells treated with 30 μM norgestimate were not changed compared to untreated cells. Therefore, norgestimate is not a PAR antagonist and TRPC4 and TRPC5 activation via PAR stimulation is suitable to measure the channels inhibition by norgestimate.

30 μM norgestimate had only small inhibitory effects on TRPC4 and TRPC5 (FIG. 2 A, C). An $IC_{50}>30$ μM was determined on both TRPC4 (n=2, FIG. 2 B) and TRPC5 (n=4, FIG. 2 D).

In summary these FLIPR measurements have shown that norgestimate inhibits channels of the TRPC3/6/7 subfamily as well as of the TRPC4/5 subfamily when applied in micromolar concentrations. Norgestimate was more effective on the TRPC3/6/7 than on the TRPC4/5 subfamily. Therefore, norgestimate was chosen for further experiments to test its discriminating capability.

2. Patch Clamp Recordings
2.1. Differential Effect of Norgestimate on Recombinant Homomeric TRPC5 and TRPC6 Channels Inhibition of TRPC6- and TRPC5-mediated $Ca^{2+}$-influx by norgestimate monitored in fluorometric experiments with cell populations was validated and compared with whole-cell patch clamp recordings of single cells. Channels were indirectly excited with the same stimulus for better comparability of the norgestimate effect. Aluminium tetrafluoride ($AlF_4^-$) applied intracellularly via the patch pipette activates G-proteins by mimicking GTP (Sternweis & Gilman, 1982; Bigay et al., 1987). Subsequently TRPC channels are stimulated and mediate non-specific cationic currents (FIG. 3 A, B) When 10 μM norgestimate were applied to activated TRPC6 channels, 89.9 ±3.1% (n=15) of the current measured at resting membrane potential was blocked. This inhibition was reversible as current amplitude increased after norgestimate wash out (FIG. 3 A). The adjacent block by 10 μM lanthanum ($La^{3+}$) was complete and reversible and thus used for background (leak) calculation.

By contrast, application of 10 μM norgestimate to stimulated TRPC5 channels had a minor effect on the current, 25.9±5.7% (n=20) were blocked. Since these channels are potentiated by micromolar $La^{3+}$ concentrations (Jung et al., 2003), 2-aminoethoxydiphenyl borate (2-APB), a characterized TRPC5 blocker (Xu et al., 2005) was used instead. Background was calculated by application of 10 μM 2-APB that completely and reversibly blocked the channel.

So far all norgestimate effects were investigated on homomeric channels heterologously expressed in HEK293 cells. It is well known that TRPC channels heteromultimerize under physiological conditions (reviewed by Schaefer, 2005). Taking the numerous possible stoichiometrically compositions of these heteromultimers into account, it is common use to start pharmacological examinations of TRPC channels in artificial model systems. But it is even more interesting to test whether norgestimate inhibits native TRPC channels too.

2.2 Effect of Norgestimate on Native Heteromeric TRPC6/7 Channels

Figure 4:
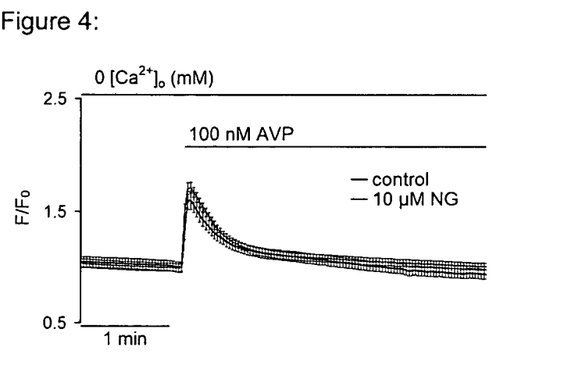
FIG. 4:
Time-dependent changes of $[Ca^{2+}]_i$ of fura-2-loaded A7r5 cells. Cells were preincubated with or without (control) 10 μM norgestimate (NG) in calcium-free standard extracellular solution (1 mM EGTA) for 5 min before stimulating the V1 receptor by application of 100 nM AVP. Data are represented as means of 33 cells (control) and 36 cells (10 μM norgestimate).
Measurements were performed using a standard imaging setup (TILL Photonics, Gräfelfing, Germany).

The A7r5 cell line (derived from rat thoracic aorta smooth muscle cells) is a model system to investigate endogenous TRPC channels (Jung et al., 2002; Soboloff et al., 2005). The channels were indirectly stimulated by $Arg^8$-vasopressin (AVP), a vasoconstricting peptide that activates the endogenous vasopressin $V_{1A}$ receptor in these cells (Thibonnier et al., 1991). Before whole-cell patch clamp recordings were performed, it was shown in calcium imaging experiments that norgestimate does not generally suppress V1 receptors (FIG. 4)

Figure 5:
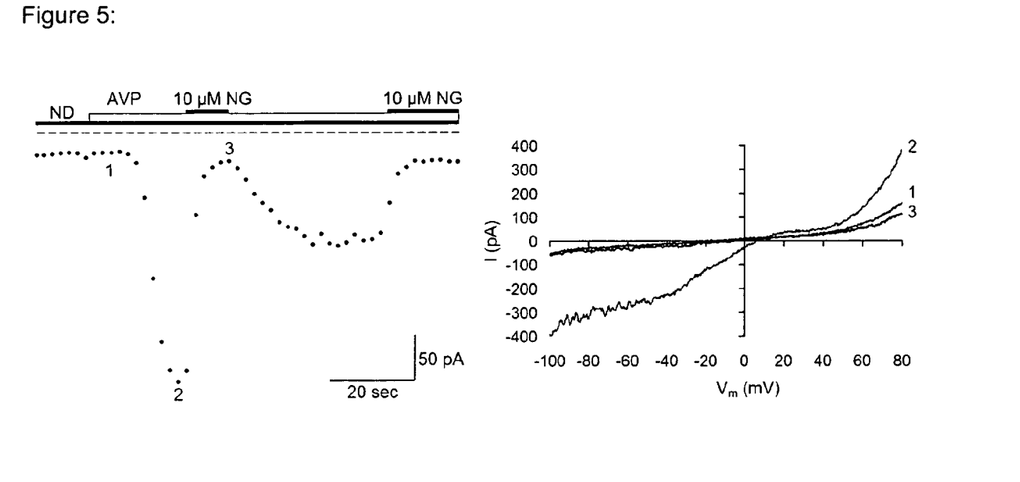
FIG. 5:
Effect of 10 μM norgestimate (NG) on whole-cell currents evoked by 100 nM AVP on A7r5 cells in standard extracellular solution (200 μM $[Ca^{2+}]_o$). Whole cell currents recorded at −60 mV (left panels) and the corresponding I-V relationships are shown (right panels). The curves were obtained during voltage ramps from −100 to +80 mV. L-type voltage-gated $Ca^{2+}$ channels were blocked by 5 μM nimodipine (ND) during the whole experiment.

Perfusion of A7r5 cells with 100 nM AVP stimulated non-selective cationic currents that bore the biophysical hallmarks of TRPC channels (FIG. 5). The double-rectifying I-V relationship was similar to those exhibited by the heterologously expressed TRPC6 homomers (FIG. 3 A). When 10 μM norgestimate were applied to AVP-stimulated A7r5 cells, 86.5±6.0% (n=8) of the current measured at resting membrane potential were blocked and this effect was reversible (FIG. 5).

The invention claimed is:

1. A method for selectively inhibiting a transient receptor potential channel (TRPC) ion channel comprising contacting a cell expressing a TRPC ion channel with norgestimate.

2. The method according to claim 1, wherein the TRPC ion channel is selected from the group consisting of: TRPC3, TRPC6, and TRPC7.

3. The method according to claim 1, wherein the method is performed in vitro.

4. The method according to claim 1, wherein the method is performed in vivo in a non-human animal.

5. The method according to claim 4, wherein the animal is a mouse or a rat.

6. A method for determining the effect of norgestimate on transient receptor potential channel (TRPC) ion channel activity comprising:
   a) contacting a cell expressing a TRPC ion channel with norgestimate, and
   b) measuring or detecting a change of the TRPC ion channel activity.

7. The method according to claim 6, wherein the cell is a fluorescent cell.

8. The method according to claim 6, wherein the cell is selected from the group consisting of a MDCK cell, a HEK 293 cell, a HEK 293 T cell, a BHK cell, a COS cell, a NIH3T3 cell, a Swiss3T3 cell, and a CHO cell.

9. The method according to claim 6, wherein the TRPC ion channel activity is measured or detected by measuring or detecting a change in $Ca^{2+}$ flux by a process selected from the group consisting of patch clamp techniques, whole cell currents, radiolabeled ion fluxes, and fluorescence using voltage-sensitive dyes or ion-sensitive dyes.

10. A method for profiling the selectivity of norgestimate for a transient receptor potential channel (TRPC) ion channel comprising:
    assessing norgestimate's ability to inhibit TRPC ion channel activity, and comparing the inhibition potency of norgestimate between and within the different TRPC subfamilies.

* * * * *